(12) United States Patent
Naka et al.

(10) Patent No.: US 12,109,517 B2
(45) Date of Patent: Oct. 8, 2024

(54) EXOSOME EXTRACTION DEVICE AND EXOSOME EXTRACTION METHOD

(71) Applicant: SHIBUYA CORPORATION, Kanazawa (JP)

(72) Inventors: Toshiaki Naka, Kanazawa (JP); Shigeki Koishi, Kanazawa (JP); Akira Hatanaka, Kanazawa (JP)

(73) Assignee: SHIBUYA CORPORATION, Kanazawa (JP)

( * ) Notice: Subject to any disclaimer, the term of this patent is extended or adjusted under 35 U.S.C. 154(b) by 529 days.

(21) Appl. No.: 17/196,327

(22) Filed: Mar. 9, 2021

(65) Prior Publication Data

US 2021/0291083 A1   Sep. 23, 2021

(30) Foreign Application Priority Data

Mar. 23, 2020  (JP) ................. 2020-051749

(51) Int. Cl.
 *B01D 29/56* (2006.01)
 *B01D 29/62* (2006.01)
 *B01D 61/14* (2006.01)

(52) U.S. Cl.
 CPC ............. *B01D 29/56* (2013.01); *B01D 29/62* (2013.01); *B01D 61/145* (2013.01);
 (Continued)

(58) Field of Classification Search
 CPC ...... B01D 29/56; B01D 29/62; B01D 61/145; B01D 2201/085; B01D 2201/088; B01D 2311/2649; B01D 2311/2692
 (Continued)

(56) References Cited

U.S. PATENT DOCUMENTS

| 2004/0241176 A1 | 12/2004 | Lamparski et al. |
| 2011/0309018 A1* | 12/2011 | Kopf ............. B01D 61/58 210/639 |
| 2020/0071748 A1 | 3/2020 | Kim |

FOREIGN PATENT DOCUMENTS

| JP | 2003531864 A | 10/2003 |
| JP | 2019527702 A | 10/2019 |
| JP | 2020501562 A | 1/2020 |

OTHER PUBLICATIONS

Heinemann et al., Benchtop isolation and characterization of functional exosomes by sequential filtration, Journal of Chromatography A, vol. 1372, (2014), pp. 125-135.*

(Continued)

*Primary Examiner* — Jennifer M. H. Tichy
(74) *Attorney, Agent, or Firm* — FLYNN THIEL, P.C.

(57) ABSTRACT

A liquid containing exosomes is filtered through a first filter that has a hole diameter that passes the exosomes and blocks cells, and is then stored in a first storage unit (rough filtration step). Next, pressure is applied to the inside of the first storage unit to pump the liquid to a pre-filtration chamber in a second filter that blocks the exosomes so that water in the liquid is filtered out into a post-filtration chamber. The exosome-containing liquid that was not filtered out is returned to the first storage unit, thereby increasing the exosome concentration in the liquid for extraction (concentration step). The exosome-containing concentrate in the first storage unit is then filtered through a third filter having a hole diameter that passes the exosomes and blocks bacteria, and is sent to a recovery unit (sterilization filtration step).

6 Claims, 6 Drawing Sheets

(52) U.S. Cl.
CPC .. *B01D 2201/085* (2013.01); *B01D 2201/088* (2013.01); *B01D 2311/2649* (2013.01); *B01D 2311/2692* (2013.01)

(58) Field of Classification Search
USPC ...................................................... 435/317.1
See application file for complete search history.

(56) References Cited

OTHER PUBLICATIONS

Tankeshwar, Size of Bacteria: Giant, Smallest, and Regular Ones, General Microbiology, Last updated Dec. 18, 2022, Available online at: microbeonline.com/size-of-bacteria/.*

* cited by examiner

EXOSOME EXTRACTION DEVICE AND EXOSOME EXTRACTION METHOD

FIELD OF THE INVENTION

The present invention relates to an exosome extraction device and an exosome extraction method, particularly to an exosome extraction device for extracting exosomes from an exosome-containing liquid and an exosome extraction method.

DESCRIPTION OF THE RELATED ART

Today, exosomes secreted from cells are used in the fields of cancer and pulmonary fibrosis treatment, beauty, and food. Such exosomes can be extracted from a liquid containing cells such as blood and stem cells of adipocyte origin, and various methods for this are known (Japanese Publication No. 2020-501562, Japanese Publication No. 2019-527702, and Japanese Publication No. 2003-531864).

In Japanese Publication No. 2020-501562, exosomes are separated by ultra-high-speed centrifugation of a liquid containing the exosomes. In Japanese Publication No. 2019-527702 and Japanese Publication No. 2003-531864, the liquid containing the exosomes is filtered out using a plurality of filters having different hole diameters and is gradually concentrated while removal of residues of cell origin in the liquid, thereby extracting the exosomes.

However, in the method using the ultracentrifugal method of Japanese Publication No. 2020-501562, only about several hundreds of micro milliliters can be obtained by one operation, and the recovery rate is low (about 20 to 30%).

Besides, even in the methods of Japanese Publication No. 2019-527702 and Japanese Publication No. 2003-531864, exosome extraction still consumes time, which means they are not suitable for mass production, and a device or method for obtaining a large amount of exosomes more efficiently is required.

To solve such a problem, the present invention provides an exosome extraction device and an exosome extraction method that enable efficient mass-extraction of exosomes.

SUMMARY OF THE INVENTION

In particular, an exosome extraction device according to a first aspect is characterized by: a stock solution supply unit that supplies a liquid composed of a cell culture supernatant containing exosomes; a first storage unit that stores the liquid supplied from the stock solution supply unit; a first filter that is provided between the stock solution supply unit and the first storage unit and has a hole diameter that passes the exosomes and blocks cells; a second filter that blocks the exosomes, and has a pre-filtration chamber into which the exosome-containing liquid flows, and a post-filtration chamber for storing the filtered liquid; a circulation path that consists of a supply path and a return path provided between the first storage unit and the pre-filtration chamber of the second filter; a discharge path that is connected to the post-filtration chamber of the second filter; a recovery unit for recovering the liquid contained in the first storage unit; and a third filter that is provided between the first storage unit and the recovery unit and has a hole diameter that passes the exosomes and blocks bacteria, wherein the liquid in the stock solution supply unit is filtered through the first filter and is sent to the first storage unit, the liquid in the first storage unit is then circulated in the circulation path to concentrate the exosome-containing liquid through the second filter, and the exosome-containing concentrate liquid in the first storage unit is filtered through the third filter and is sent to the recovery unit.

An exosome extraction method according to a third aspect is characterized by: filtering a liquid composed of a cell culture supernatant containing exosomes through a first filter that has a hole diameter that passes the exosomes and blocks cells, and then storing the liquid in the first storage unit; and sending the liquid from the first storage unit to a pre-filtration chamber in the second filter that blocks the exosomes so that unnecessary components in the liquid are filtered out into the post-filtration chamber, and returning the exosome-containing liquid that was not filtered out and remains in the pre-filtration chamber to the first storage unit, thereby forming a circulation path between the first storage unit and the second filter and increasing the exosome concentration in the liquid, filtering the exosome-containing concentrate in the first storage unit through a third filter having a hole diameter that passes the exosomes and blocks bacteria, and sending the concentrate to a recovery unit to extract the exosomes.

According to the first and third aspects of the invention, an exosome-containing liquid obtained from a cell culture supernatant is filtered through the first filter, so that the exosome-containing liquid from which cells and the like have been removed can be sent to a first storage unit.

After that, the liquid in the first storage unit is sent to the second filter, unnecessary components in the liquid are filtered out into a post-filtration chamber, and the unfiltered exosome-containing liquid remaining in a pre-filtration chamber is returned to the first storage unit for concentration.

Since a circulation path is formed by the first storage unit and the second filter in this way, unnecessary components are gradually discharged from the liquid and exosome concentration in the liquid increases, so that exosomes are extracted.

Filtering the concentrate in which exosomes are concentrated through the third filter and recovering it into a recovery unit in this way maintains the sterile state and enables extraction of exosomes that can be clinically used.

The present invention makes it possible to process a large amount of exosome-containing liquid as described above, and thus extract a larger amount of exosomes more efficiently than in Japanese Publication No. 2020-501562, Japanese Publication No. 2019-527702, and Japanese Publication No. 2003-531864. In addition, the extracted exosome concentrate is maintained in a sterile state and can be clinically used.

DETAILED DESCRIPTION OF THE PREFERRED EMBODIMENTS

Figure 1:
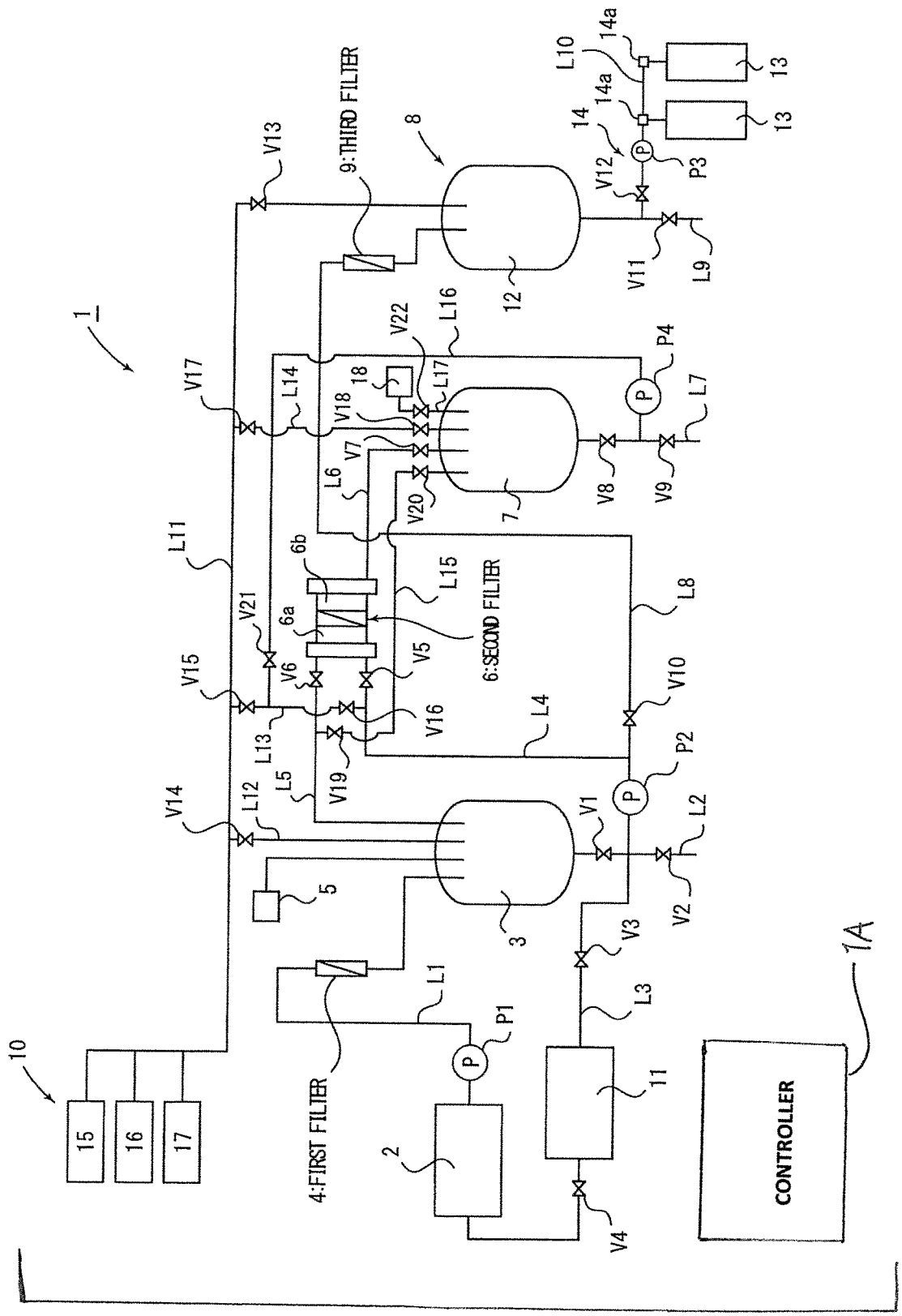
FIG. 1 is a circuit diagram of an exosome extraction device according to one embodiment.

To explain the embodiments illustrated below, FIG. 1 shows an exosome extraction device 1 according to this embodiment that extracts and recovers exosomes from a liquid obtained by culturing blood, stem cells of adipocyte origin, cells of tissue origin, and the like collected from humans or mammals.

Here, the exosomes are fine particles surrounded by a membrane component having a diameter of about 40 to 150 nm secreted from cells, and are known to contain micro RNAs and proteins that affect other cells.

Recent studies have shown that the exosomes are used not only for cancer diagnosis and treatment but also in the fields of beauty and food, and technology for efficiently collecting a large amount of exosomes is required for these purposes. Since the exosomes are described in detail in Japanese Publication No. 2020-501562, Japanese Publication No. 2019-527702, and Japanese Publication No. 2003-531864, their detailed description will be omitted.

The exosome extraction device 1 includes a stock solution supply unit 2 for supplying a liquid (cell culture supernatant) containing exosomes, a first storage unit 3 for storing the liquid supplied from the stock solution supply unit 2, a first filter 4 provided between the stock solution supply unit 2 and the first storage unit 3, a positive pressure load unit 5 for applying pressure to the inside of the first storage unit 3, a second filter 6 for filtering the liquid from the first storage unit 3, a second storage unit 7 for storing the exosome-free liquid obtained by filtration through the second filter 6, a recovery unit 8 for recovering the liquid from which the exosomes have been extracted, and a third filter 9 provided between the first storage unit 3 and the recovery unit 8, and a sterilization and cleaning unit 10 for sterilizing and cleaning the storage unit and the filter constituting the exosome extraction device 1, which are controlled by a controller 1A shown diagrammatically in the drawing.

With the exosome extraction device 1 having the aforementioned configuration, the cell culture supernatant (from which cells larger than exosomes have been removed using the first filter 4) is stored in the first storage unit 3, the exosome-containing liquid is then circulated between the first storage unit 3 and the second filter 6 so that the water in the liquid is discharged to increase the exosome concentration, and finally, the mixed bacteria are removed using the third filter 9 when the liquid containing concentrated exosomes is recovered using the recovery unit 8.

The stock solution supply unit 2 is supplied with, as a cell culture supernatant, a liquid obtained by culturing blood, stem cells of adipocyte origin, cells of each tissue, mesenchymal stem cells, or the like collected from a human body or a mammal, and although not shown in the drawing, has a configuration in which a bag containing the cell culture supernatant can be connected to a plurality of ports.

A first path L1 is provided between the stock solution supply unit 2 and the first storage unit 3, a first liquid feeding pump P1 is provided on the first path L1, and the first filter 4 is provided downstream from the first liquid feeding pump P1.

The first storage unit 3 is provided so that the inside can be hermetically sealed, and is provided with an air vent valve (not shown in the drawing) for discharging internal air when a liquid is supplied.

The first path L1 is connected to an upper part of the first storage unit 3, and a second path L2 for drainage is provided to a lower part of the first storage unit 3, and first and second on-off valves V1 and V2, which are controlled by the controller 1A, are provided on the upstream side and the downstream side from the second path L2, respectively.

A third path L3 is connected to the second path L2 between the first on-off valve V1 and the second on-off valve V2, and the other end of the third path L3 is connected to the stock solution supply unit 2.

A saline supply unit 11 containing a saline is provided on the third path L3, and third and fourth on-off valves V3 and V4, which are controlled by the controller 1A, are provided in the positions adjacent to the upstream side and the downstream side of the saline supply unit 11, respectively.

The first filter 4 has a hole diameter that passes exosomes in the liquid and blocks cells or the like in the liquid. To be specific, the filter has a hole diameter of 0.22 µm.

The first filter 4 filters cells and other impurities from the cell culture supernatant that is supplied from the stock solution supply unit 2 and flows through the first path L1, and passes the exosomes contained in the cell culture supernatant so that they are supplied to the first storage unit 3.

Note that a filter having a hole diameter of 5 µm, 3 µm, or 1 µm may be used instead to capture cells, and a filter having a hole diameter of 0.1 µm can be used instead depending on the size of the exosome to be extracted. For this reason, it is desirable to adopt a filter having a hole diameter of 0.1 µm to 5 µm as the first filter.

The positive pressure load unit 5 is connected to the first storage unit 3 through a pipe, and an air supply to the inside of the first storage unit 3 increases the internal pressure in the first storage unit 3, thereby preventing the mixing of external bacteria.

The positive pressure load unit 5 of this embodiment supplies, for example, high pressure air at 0.3 MPa higher than atmosphere to the first storage unit 3.

The second filter 6 is provided in a housing having a required capacity, and the second filter 6 has a pre-filtration chamber 6a in which the liquid from the first storage unit 3 flows in the housing, and a post-filtration chamber 6b that houses the filtered liquid.

A fourth path L4 as a supply path and a fifth path L5 as a return path are connected between the pre-filtration chamber 6a and the first storage unit 3. The upstream end of the fourth path L4 is connected between the first on-off valve V1 and the second on-off valve V2 on the second path L2, and the downstream end of the fifth path L5 is connected to the upper part of the first storage unit 3.

The fourth path L4 and the fifth path L5 are provided with fifth and sixth on-off valves V5 and V6 controlled by the controller 1A, respectively, and the fourth path L4 is also provided with a second liquid feeding pump P2.

A sixth path L6 is provided between the post-filtration chamber 6b and the second storage unit 7, and a seventh on-off valve V7 controlled by the controller 1A is provided on the sixth path L6.

The second filter 6 which is ultrafiltration membrane blocks exosomes in the liquid and passes medium components smaller than exosomes, and unnecessary components such as proteins. To be specific, the filter has a 3 kDa NMWL (Nominal Molecular Weight Limit).

With such a configuration, the liquid flowing from the first storage unit 3 into the pre-filtration chamber 6a of the second filter 6 through the fourth path L4 is filtered through the second filter 6, but the exosomes in the liquid cannot pass through the second filter 6 and remains in the pre-filtration chamber 6a, and then returns to the first storage unit 3 via the fifth path L5.

In other words, the first storage unit 3 and the second filter 6 of this embodiment form a circulation path with the fourth path L4 as a supply path and the fifth path L5 as a return path. Exosomes that were blocked by the second filter 6 circulate in this circulation path.

The liquid composed of unnecessary components and containing no exosomes and flowing into the post-filtration chamber 6*b* is then discharged to the second storage unit 7 via the sixth path L6.

The second filter only has to have a hole diameter that blocks the exosomes to be extracted, and can be any filter other than 3 kDa filters.

The second storage unit 7 comprises a closed tank that can contain liquid, and the sixth path L6 is connected to an upper part of the second storage unit 7 and a seventh path L7 is connected to a lower part of the second storage unit 7 for discharging the liquid from the second storage unit 7. The seventh path L7 is provided with eighth and ninth on-off valves V8 and V9 controlled by the controller 1A on the upstream side and the downstream side, respectively.

The recovery unit 8 comprises a third storage unit 12 that can contain liquid and a distribution unit 14 connected to the third storage unit 12 and connectable to a plurality of bags 13 of a predetermined capacity.

An eighth path L8 as a recovery path is connected between the third storage unit 12 and the first storage unit 3, and the third filter 9 is provided on the eighth path L8.

The upstream end of the eighth path L8 is connected between the first on-off valve V1 and the second on-off valve V2 on the second path L2, and a tenth on-off valve V10 controlled by the controller 1A is provided in a position of the eighth path L8 adjacent to the connection position.

The eighth path L8 as the recovery path only has to be connected to the circulation path comprising the first storage unit 3 and the second filter 6, and may be connected to, for example, the fifth path L5 as the return path.

The third storage unit 12 comprises a tank that can contain liquid, and the eighth path L8 is connected to an upper part of the third storage unit 12 and a ninth path L9 is connected to a lower part of the third storage unit 12 for discharging the liquid from the third storage unit 12. The ninth path L9 is provided with a eleventh on-off valve V11, which is controlled by the controller 1A.

The distribution unit 14 comprises a tenth path L10 connected to the upstream side of the eleventh on-off valve V11 on the ninth path L9, a twelfth on-off valve V12 provided on the tenth path L10, and a third liquid feeding pump P3 provided on the downstream side of the twelfth on-off valve V12, and a plurality of connection ports 14*a* provided on the downstream side of the third liquid feeding pump P3.

When the third liquid feeding pump P3 is operated while the eleventh on-off valve V11 on the ninth path L9 is closed and the twelfth on-off valve V12 on the tenth path L10 is open, the liquid contained in the third storage unit 12 is distributed to the bags 13 connected to the connection ports 14*a*.

The third filter 9 provided on the fifth path L5 has a hole diameter that passes exosomes and blocks bacteria, and may be a filter having a hole diameter of 0.22 μm like the first filter 4.

The exosome concentrate liquid obtained by circulation between the first storage unit 3 and the second filter 6 flows through the fifth path L5 and is recovered into the third storage unit 12 of the recovery unit 8, but is filtered through the third filter 9 while flowing through the fifth path L5.

Filtration with the liquid with the third filter 9 allows the exosome-containing liquid to be supplied to the recovery unit 8 in a sterile state, and the extracted exosomes can be safely recovered into the bags 13.

Note that the third filter 9 may be a 0.1-μm filter depending on the size of the exosome to be extracted. Thus, the third filter can be a filter of 0.1 μm to 0.3 μm.

To explain the sterilization and cleaning unit 10 now, in the exosome extraction device 1 of this embodiment, before the extraction operation is started or upon completion of the exosome recovery operation in the recovery unit 8, the aforementioned first to third storage units 3, 7, and 12 and other pipes and the like constituting the exosome extraction device 1 are sterilized by heated steam.

However, since the second filter 6 cannot be sterilized with heated steam, the second filter 6 is cleaned with a chemical solution in this embodiment.

The sterilization and cleaning unit 10 includes an air supply unit 15 for supplying sterile air, a steam supply unit 16 for supplying heated steam, a cleaning solution supply unit 17 for supplying cleaning solution such as injection water, pyrogen-free water, and sterile water, and a chemical agent supply unit 18 for supplying the stock solution of the chemical agent to the second storage unit 7.

Of these, the air supply unit 15, the steam supply unit 16, and the cleaning solution supply unit 17 are connected to the eleventh path L11, and the downstream end of the eleventh path L11 is connected to an upper part of the third storage unit 12. A thirteenth on-off valve V13 controlled by the controller 1A is provided in a position adjacent to the third storage unit 12 on the eleventh path L11.

The twelfth, thirteenth, and fourteenth paths L12, L13, and L14 are branched and connected to the eleventh path L11. The twelfth path L12 is connected to an upper part of the first storage unit 3. A fourteenth on-off valve V14 controlled by the controller 1A is provided on the twelfth path L12.

The thirteenth path L13 is connected to a position adjacent to the upstream side of the fifth on-off valve V5 on the fourth path L4, and fifteenth and sixteenth on-off valves V15 and V16 controlled by the controller 1A are provided on the thirteenth path L13.

The fourteenth path L14 is connected to an upper part of the second storage unit 7, and seventeenth and eighteenth on-off valves V17 and V18 controlled by the controller 1A are provided on the fourteenth path L14.

A fifteenth path L15 is connected between the fifth path L5 and the second storage unit 7. To be specific, one end of the fifteenth path L15 is connected to a position adjacent to the downstream side of the sixth on-off valve V6 provided on the fifth path L5, and the other end is connected to an upper part of the second storage unit 7. The fifteenth path L15 is provided with nineteenth and twentieth on-off valves V19 and V20 controlled by the controller 1A.

On the other hand, a sixteenth path L16 is also provided between the seventh path L7 and the thirteenth path L13. To be specific, one end of the sixteenth path L16 is connected between the eighth on-off valve V8 and the ninth on-off valve V9 on the seventh path L7, and the other end is connected between the fifteenth on-off valve V15 and the sixteenth on-off valve V16 on the thirteenth path L13. The sixteenth path L16 is provided with a fourth liquid feeding pump P4 and a twenty-first on-off valve V21 controlled by the controller 1A.

The chemical agent supply unit 18 is connected to an upper part of the second storage unit 7 through the seventeenth path L17, and the seventeenth path L17 is provided with a twenty-second on-off valve V22 controlled by the controller 1A.

The operation of extracting exosomes using the exosome extraction device 1 with the aforementioned configuration will now be explained with reference to FIGS. 2 to 6. For the on-off valves V shown in the drawing, white ones indicate the open state, and black ones indicate the closed state.

Figure 2:
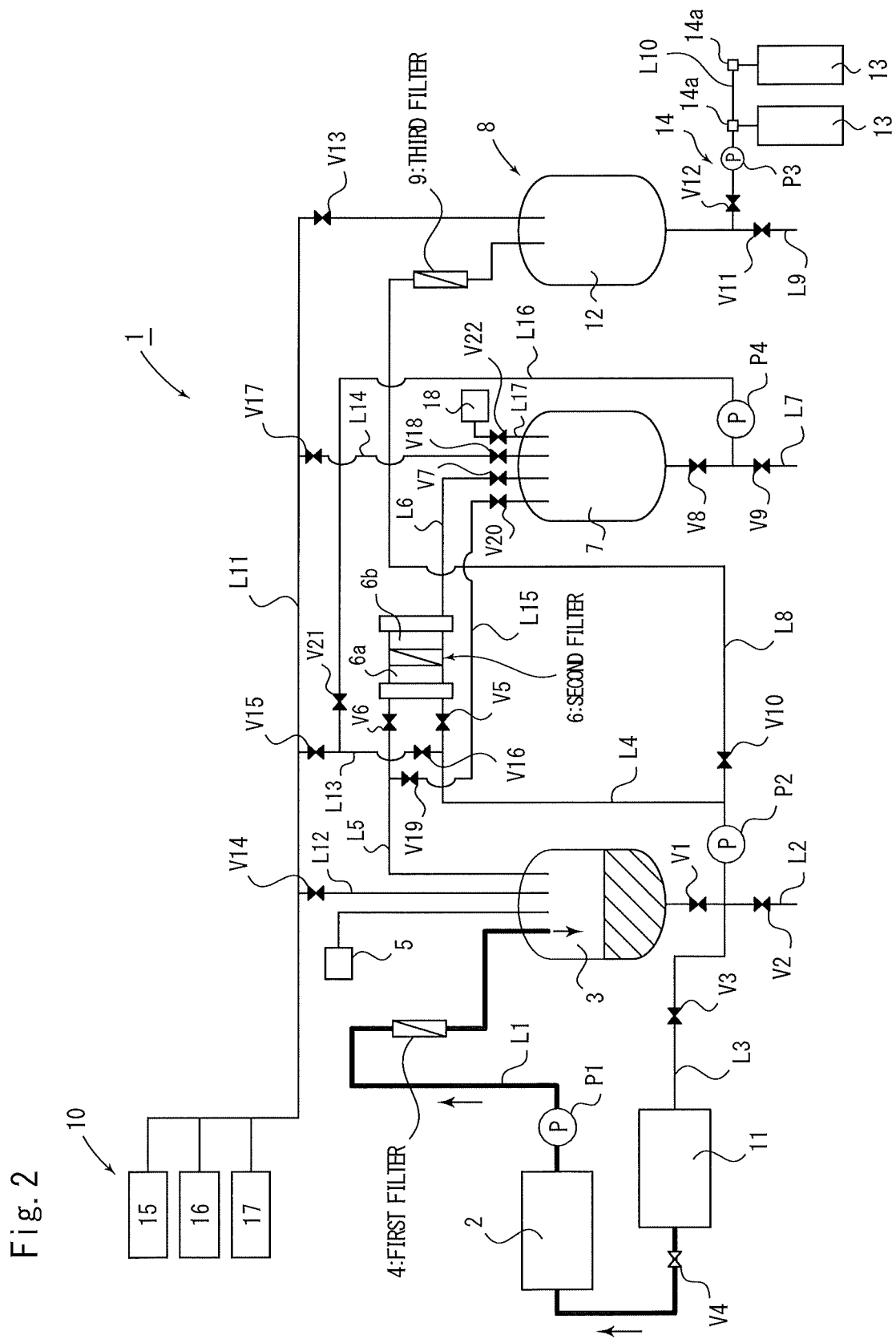
FIG. 2 is a flow diagram illustrating a rough filtration step.

FIG. 2 shows the rough filtration step of removing cells and the like from the cell culture supernatant through the first filter 4 while supplying the cell culture supernatant containing exosomes from the stock solution supply unit 2 to the first storage unit 3.

First, the stock solution supply unit 2 is supplied with the cell culture supernatant obtained by culturing blood, stem cells of adipocyte origin, cells of tissues, mesenchymal stem cells, and the like collected from a human body or a mammal. Here, for example, 10 L of cell culture supernatant is stored in the stock solution supply unit 2.

Subsequently, the first liquid feeding pump P1 provided adjacent to the stock solution supply unit 2 is operated, and the cell culture supernatant in the stock solution supply unit 2 is sent toward the first storage unit 3 through the first path L1, and along the way, is filtered through the first filter 4.

The first filter 4 filters out cells other than exosomes and other foreign matters contained in the cell culture supernatant so that the exosome-containing liquid is supplied to the first storage unit 3.

When the first liquid feeding pump P1 starts to feed the liquid and 10 L of stock solution in the stock solution supply unit 2 is discharged to the first path L1, the fourth on-off valve V4 located downstream from the saline supply unit 11 on the third path L3 is opened.

As a result, the saline is sent to the first storage unit 3, passing through the stock solution supply unit 2. Accordingly, the saline pushes out all the exosome-containing liquid remaining in the first path L1 to the first storage unit 3, so that the liquid can be recovered from the total amount of cell culture supernatant supplied to the stock solution supply unit 2.

To be specific, the amount of saline fed by the first liquid feeding pump P1 is controlled taking the capacity of the first path L1, first liquid feeding pump P1, and first filter 4 into consideration so that the exosome-containing liquid does not remain in the first path L1.

Figure 3:
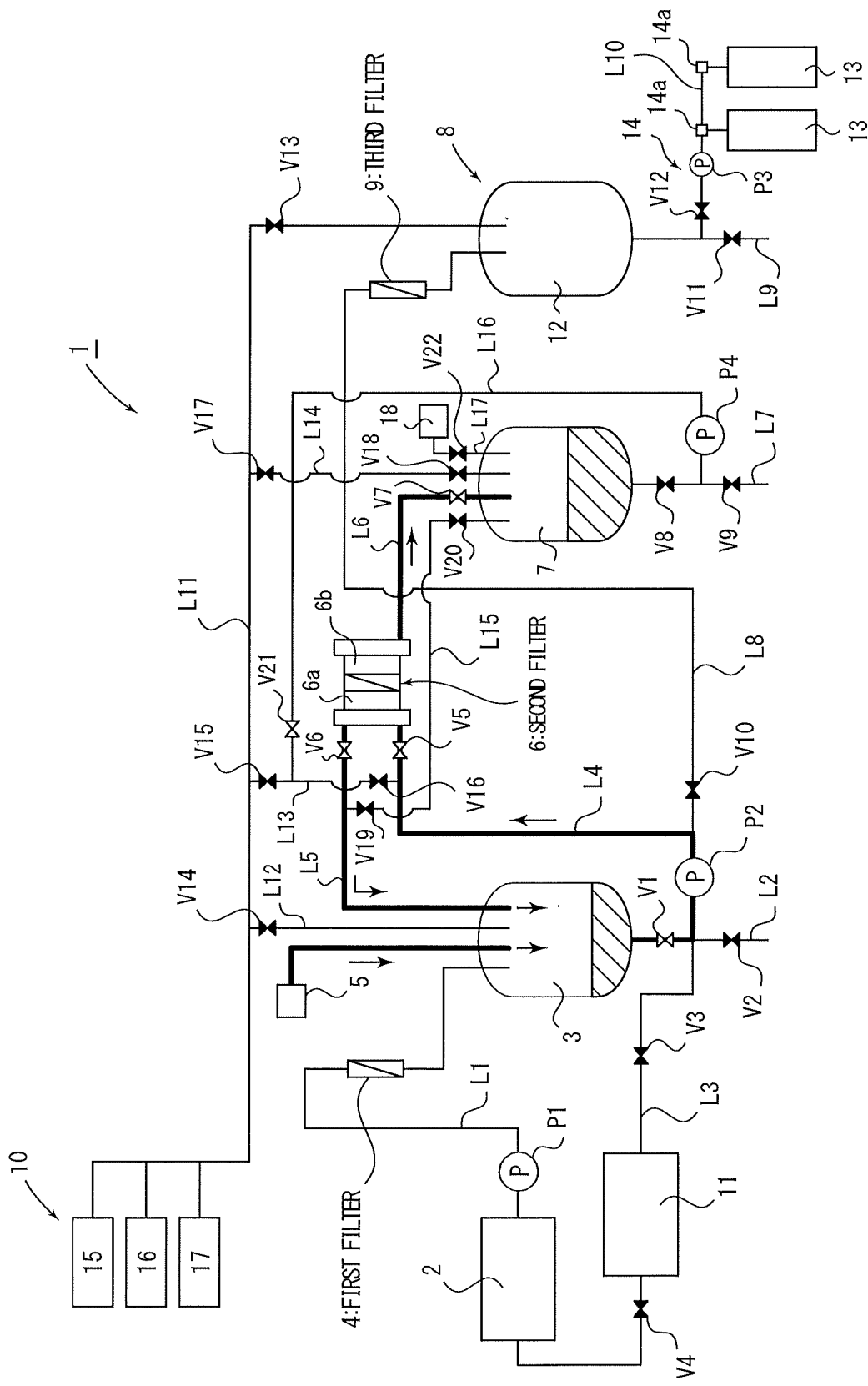
FIG. 3 is a flow diagram illustrating a concentration step.

FIG. 3 shows a concentration step in which an exosome-containing liquid is circulated between the first storage unit 3 and the second filter 6 to increase the exosome concentration in the liquid for extraction.

First, upon completion of the rough filtration step shown in FIG. 2, the controller 1A stops the first liquid feeding pump P1 on the first path L1 and closes the fourth on-off valve V4 in the third path L3.

Subsequently, high-pressure air is supplied to the first storage unit 3 through the positive pressure load unit 5 to prevent external bacteria from getting into the liquid in the first storage unit 3, the paths communicating with the first storage unit 3, and the second filter 6 during the concentration step.

In this state, the first on-off valve V1 on the second path L2 is opened to operate the second liquid feeding pump P2 on the fourth path L4 as the supply path, and the fifth on-off valve V5 on the fourth path L4 and the sixth on-off valve V6 on the fifth path L5 as a return path are opened.

Then, the exosome-containing liquid is pumped out from the first storage unit 3 to the fourth path L4 at a required pressure by the second liquid feeding pump P2 and flows into the pre-filtration chamber 6a of the second filter 6 where the liquid is filtered through the second filter 6.

At this time, since the second filter 6 blocks exosomes but passes unnecessary components other than exosomes, the exosomes in the liquid remain in the pre-filtration chamber 6a, and the unnecessary components in the liquid pass through the second filter 6 and are discharged to the post-filtration chamber 6b.

Exosomes that have not been filtered out by the second filter 6 remain in the pre-filtration chamber 6a, flow through the fifth path L5 as the return path together with the water that did not pass through the second filter 6, and return to the first storage unit 3.

Circulating the exosomes between the first storage unit 3 and the second filter 6 in this way gradually removes unnecessary components through the second filter 6, gradually increasing the exosome concentration in the liquid. This yields an exosome concentrate that has been subjected to exosome extraction.

In this embodiment, for example, when about 10 L of liquid is stored in the first storage unit 3, about 1/10 of about 1 L of exosome concentrate is obtained in the concentration step.

Finally, when it is confirmed by the level sensor (not shown) provided in the first storage unit 3 that the liquid has been concentrated to a predetermined amount, the controller 1A closes the first on-off valve V1 and opens the third on-off valve V3 on the third path L3, and then operates the second liquid feeding pump P2 so that the saline in the saline supply unit 11 is sent toward the fourth path L4.

As a result, the exosome concentrate remaining in the fourth path L4, the fifth path L5, and the second filter 6 is pushed out to the first storage unit 3 by the saline. At this time, the second liquid feeding pump P2 sends the saline in the same amount as the volumes of the fourth path L4, the fifth path L5, and the second filter 6, so that only the exosome concentrate is recovered into the first storage unit 3.

Meanwhile, the liquid composed of unnecessary components that has passed through the second filter 6 and has flowed into the post-filtration chamber 6b flows through the sixth path L6 and is stored in the second storage unit 7.

The eighth and ninth on-off valves V8 and V9 on the seventh path L7 are closed until a predetermined amount of unnecessary components are stored in the second storage unit 7. When the amount of unnecessary components in the second storage unit 7 reaches a predetermined level, the eighth and ninth on-off valves V8 and V9 are opened so that they can be discharged to a drainage tank which is not shown in the drawing.

Note that the eighth and ninth on-off valves V8 and V9 may be opened upon completion of the operation of the exosome extraction device 1, and the aforementioned unnecessary components may be directly discharged to the drainage tank from the sixth path L6 by revising the configuration of the sterilization and cleaning unit 10 as appropriate.

Figure 4:
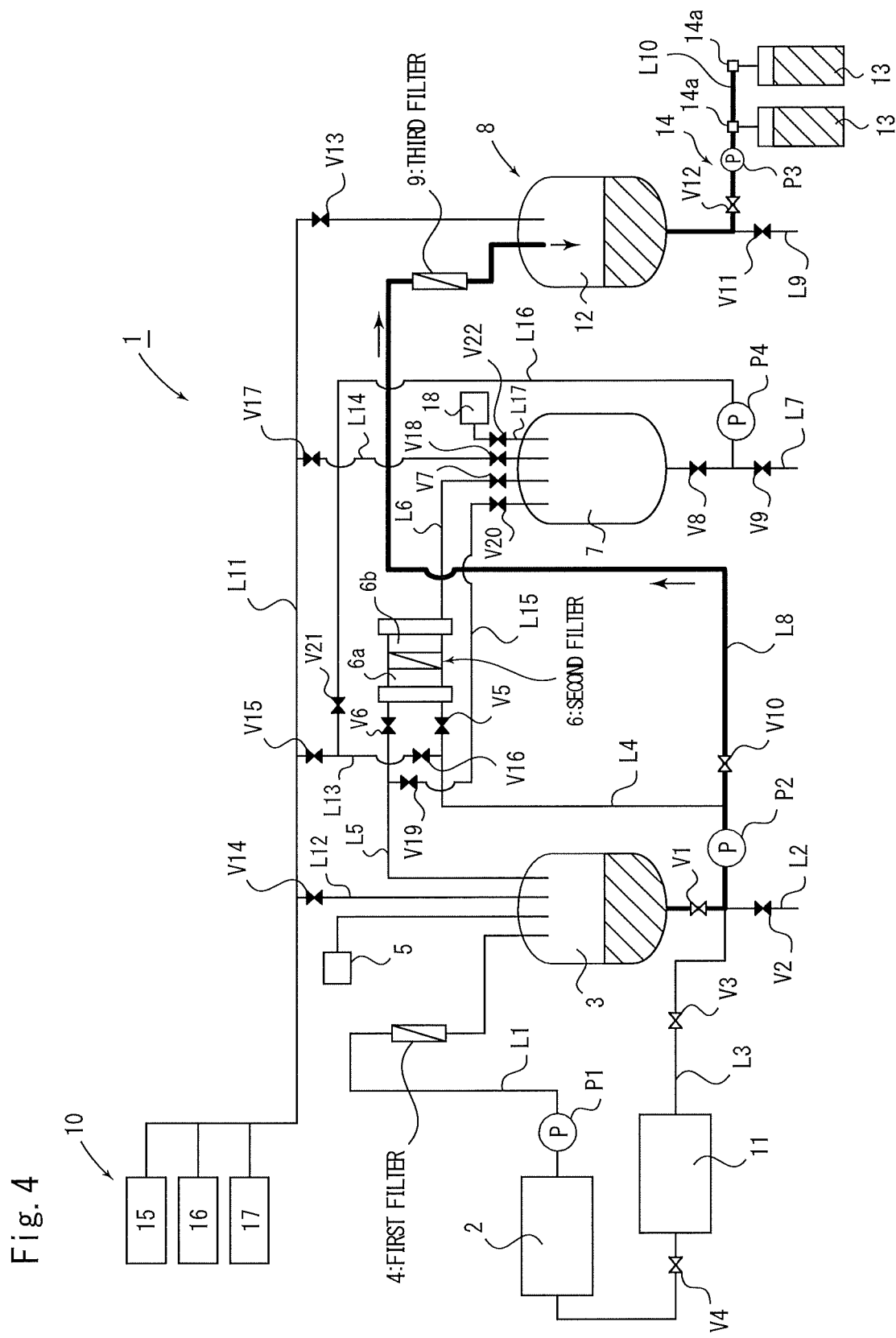
FIG. 4 is a flow diagram illustrating a sterilization filtration step.

FIG. 4 shows a filtration sterilization step in which the exosome concentrate liquid is sterilized through the third filter 9 on the way to the recovery unit 8.

Upon completion of the concentration step shown in FIG. 3, the fifth on-off valve V5 on the fourth path L4 is closed, the tenth on-off valve V10 on the eighth path L8 is opened, and the second liquid feeding pump P2 is operated, whereby the exosome concentrate liquid in the first storage unit 3 is sent to the recovery unit 8 through the eighth path L8.

At that time, the concentrate is filtered through a third filter 9 on the eighth path L8 so that bacteria mixed in the concentrate liquid is captured while the exosomes in the concentrate pass it, thereby bringing the concentrate in a sterile state.

After that, when the concentrate liquid that has passed through the third filter 9 is stored in the third storage unit 12, the twelfth on-off valve V12 on the tenth path L10 constituting the distribution unit 14 is opened to operate the third liquid feeding pump P3, so that the concentrate in the third storage unit 12 is distributed to the bags 13 connected to the connection ports 14a on the tenth path L10.

The bags 13 store the exosome extract concentrate liquid in a sterile state, and the bags 13 are detached from the connection ports 14a to complete the exosome extraction operation.

The exosome concentrate liquid in the bags 13 is maintained in an aseptic state and can therefore be used for clinical purposes and the like thereafter.

Figure 5:
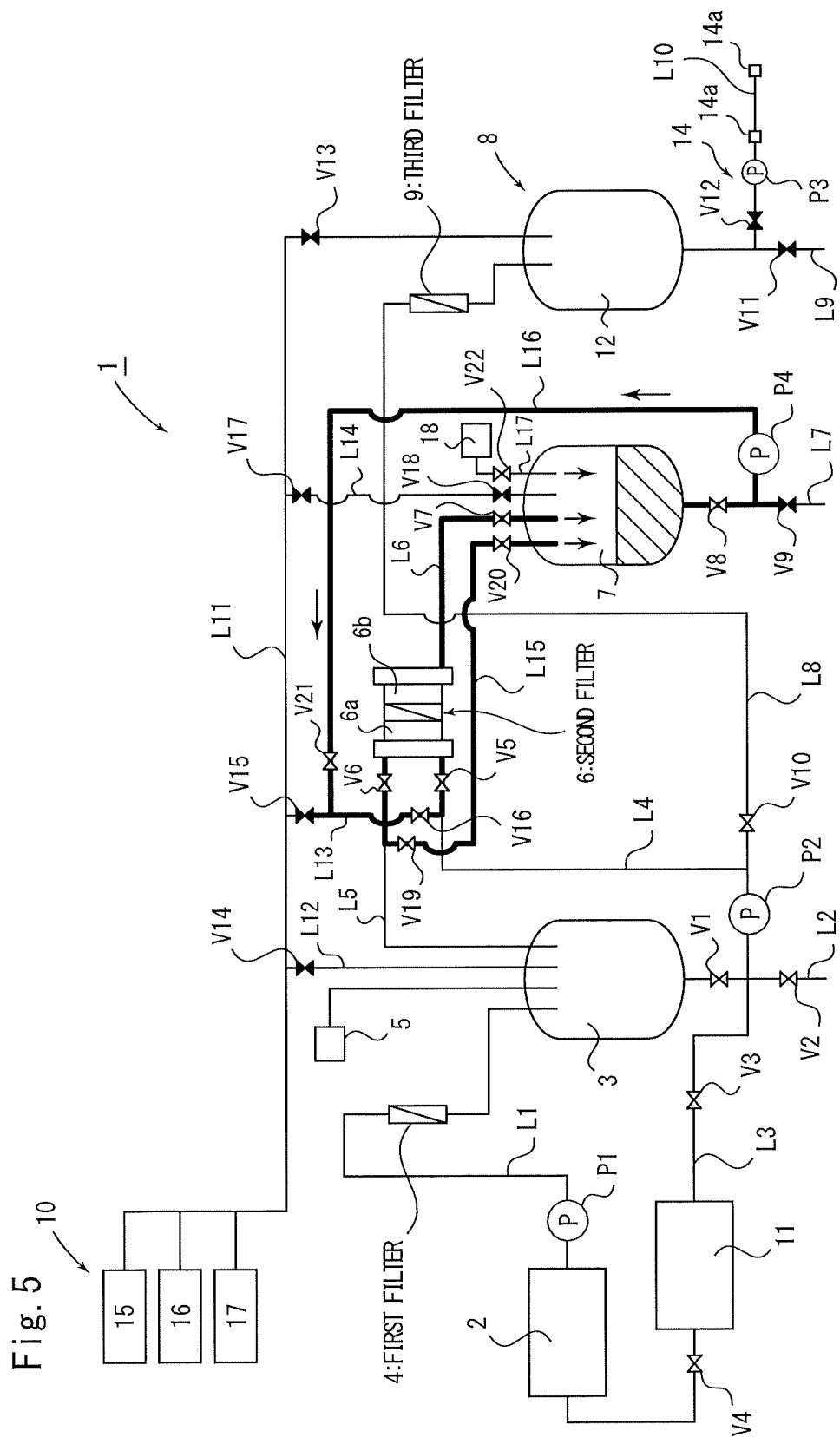
FIG. 5 is a flow diagram illustrating cleaning of a second filter in the sterilization and cleaning step.
Figure 6:
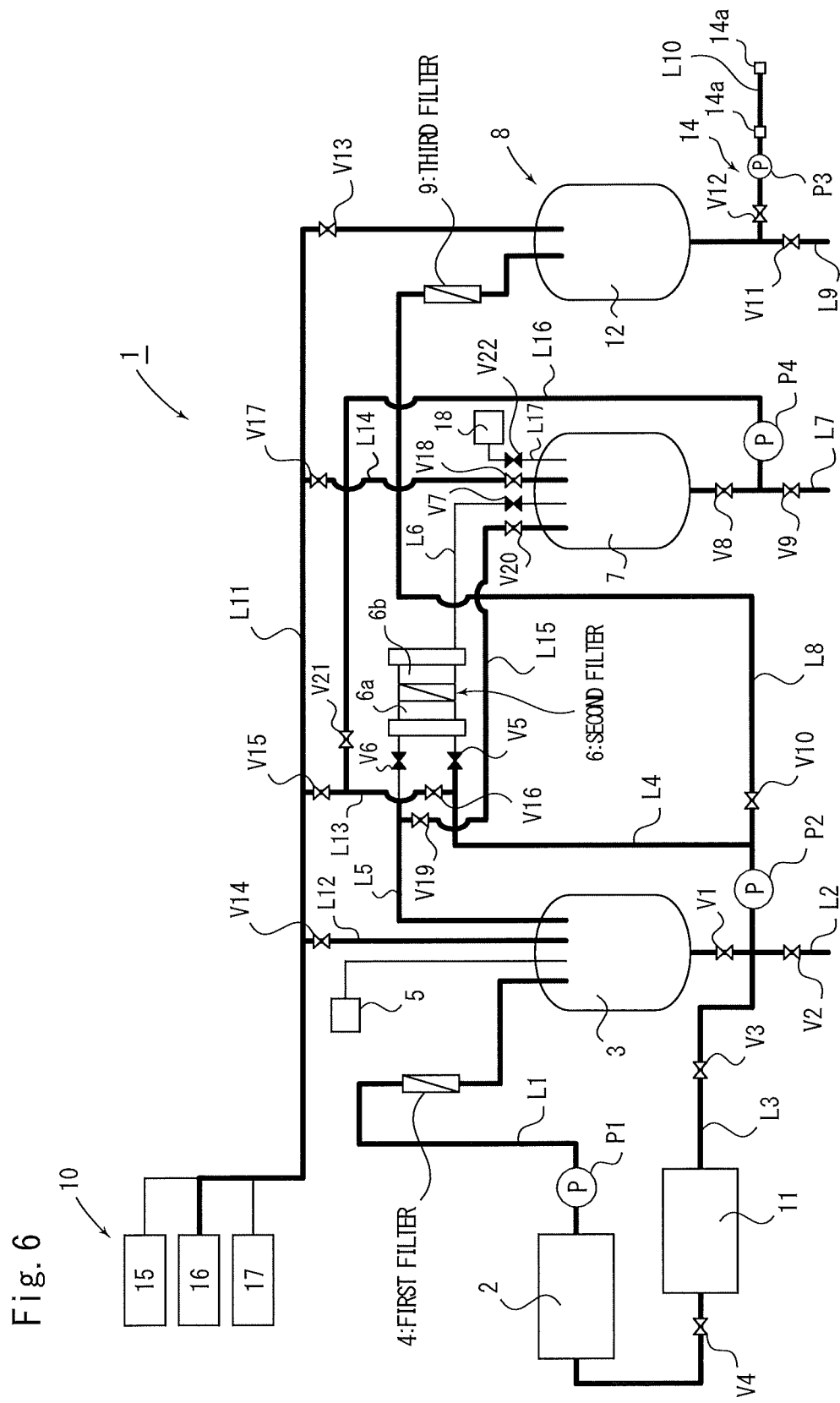
FIG. 6 is a flow diagram illustrating sterilization of other parts in the sterilization and cleaning step.

FIGS. 5 and 6 show the sterilization and cleaning step performed before and after the use of the exosome extraction device 1.

Before and after the exosome extraction operation by the exosome extraction device 1, it is necessary to clean and sterilize the storage units and filters constituting the exosome extraction device 1.

However, the second filter 6 cannot be sterilized with high-temperature steam, which means sterilization cannot be guaranteed. Thus, the second filter 6 is first cleaned with a chemical agent in the cleaning step shown in FIG. 5, and the parts other than the second filter 6 are sterilized by heated steam in the sterilization step shown in FIG. 6.

The operation after the exosome extraction operation will be explained below.

First, before the cleaning step and the sterilization step, the on-off valves on the second, seventh, and ninth paths L2, L7, and L9 connected to the lower parts of the first to third storage units 3, 7, and 12 are opened to discharge the liquids contained in the first to third storage units 3, 7, and 12.

Next, although not shown in FIG. 5, in the cleaning step, a certain amount of cleaning water is supplied to the second storage unit 7 in advance, and the stock solution of the chemical agent is supplied to the second storage unit 7 from the chemical agent supply unit 18 to prepare a cleaning solution at a predetermined concentration.

To be specific, the eighth and ninth on-off valves V8 and V9 on the seventh path L7 connected to the second storage unit 7 are opened, and the fifteenth and sixteenth on-off valves V15 and V16 on the thirteenth path L13 connected to the eleventh path L11 are opened.

At the same time, the fifth on-off valve V5 on the fourth path L4 and the sixth on-off valve V6 on the fifth path L5 are opened, and the nineteenth and twentieth on-off valves V19 and V20 on the fifteenth path L15 connected to the fifth path L5 are opened.

When the cleaning solution is sent from the cleaning solution supply unit 17 in this state, the cleaning solution flows through the eleventh path L11, the thirteenth path L13, and the fourth path L4 and flows into the pre-filtration chamber 6a of the second filter 6. After that, it flows through the fifth path L5 and the fifteenth path L15 from the pre-filtration chamber 6a into the second storage unit 7, and is discharged through the seventh path L7, accomplishing water washing.

After that, the ninth and fifteenth on-off valves V9 and V15 are closed and the seventeenth and eighteenth on-off valves V17 and V18 on the seventh path L7 are opened to supply the cleaning solution to the second storage unit 7 through the fourteenth path L14 connected to the eleventh path L11.

At the same time, the chemical agent supply unit 18 supplies the stock solution of the chemical agent to the second storage unit 7 through the seventeenth path L17, so that a cleaning solution at a predetermined concentration can be prepared.

In this state, as shown in FIG. 5, the fifteenth on-off valve V15 on the thirteenth path L13 and the seventeenth and eighteenth on-off valves V17 and V18 on the fourteenth path L14 are closed, the seventh on-off valve V7 on the sixth path L6 provided between the second filter 6 and the second storage unit 7 is opened, and the twenty-first on-off valve V21 on the sixteenth path L16 connected to the seventh path L7 is also opened.

When the fourth liquid feeding pump P4 on the sixteenth path L16 is operated, the cleaning solution prepared by the second storage unit 7 is sent to the thirteenth path L13 and the fourth path L4 through the sixteenth path L16, and is flowed into the pre-filtration chamber 6a of the second filter 6.

Then, part of the cleaning solution passes through the second filter 6 and flows into the post-filtration chamber 6b, whereby the second filter 6 is cleaned and the cleaning solution that has passed through the second filter 6 then flows through the sixth path L6 and returns to the second storage unit 7.

On the other hand, of the cleaning solution flowing into the pre-filtration chamber 6a, the cleaning solution blocked by the second filter 6 is discharged from the fifth path L5, flows through the fifteenth path L15, and returns to the second storage unit 7.

In this way, a circulation path is formed by the cleaning solution between the second filter 6 and the second storage unit 7, and the cleaning solution is circulated for a predetermined length of time to clean the portion that cannot be sterilized by the second filter 6 and the following sterilization step.

Upon completion of cleaning with the cleaning solution, a rinsing operation is performed.

To be specific, when the cleaning solution is discharged from the seventh path L7 connected to the second storage unit 7, the cleaning water from the cleaning solution supply unit 17 is supplied to the thirteenth path L13 in the same manner as the water washing procedure to perform rinsing.

Upon completion of the cleaning step shown in FIG. 5, the sterilization step shown in FIG. 6 is performed.

In the sterilization step, the fifth on-off valve V5 on the fourth path L4, the sixth on-off valve V6 on the fifth path L5, and the seventh on-off valve V7 on the sixth path L6, which are connected to the second filter 6, are closed.

When the steam supply unit 16 is operated in this state, heated steam is supplied to the first to third storage units 3, 7, and 12 through the eleventh path L11, so that the paths connected to the first to third storage units 3, 7 and 12 are also sterilized.

To be specific, part of the steam flowing into the first storage unit 3 then passes through the third path L3 and the first path L1, thereby sterilizing the first filter 4.

Similarly, part of the steam flowing into the first storage unit 3 then passes through the eighth path L8 from the second path L2, thereby sterilizing the third filter 9.

In this way, the second filter 6 and the paths other than the paths connected to the second filter 6 are sterilized with the steam. After the sterilization with the steam is completed, sterile air is supplied by the air supply unit 15 to discharge the steam.

At the time of steam sterilization, the controller 1A opens each on-off valve as appropriate so that the piping indicated by the thick lines in FIG. 6 can be sterilized.

As described above, in the exosome extraction device 1 of this embodiment, the rough filtration step shown in FIG. 2 is first performed, so that an exosome-containing liquid obtained by removing cells and the like from the cell culture supernatant through the first filter 4 can be sent to the first storage unit.

Next, the concentration step shown in FIG. 3 is performed, so that a circulation path is formed between the first storage unit 3 and the second filter 6, and the exosome concentration in the liquid contained in the first storage unit 3 can be increased by the second filter 6, allowing exosomes to be extracted efficiently.

Subsequently, the sterilization filtration step shown in FIG. 4 is performed, which allows bacteria to be removed from the exosome concentrate through the third filter 9; thus, the exosome concentrate recovered through the recovery unit 8 is immediately used for clinical purposes and the like.

Further, in the aforementioned embodiment, a large amount of liquid can be processed according to the capacity of the first storage unit 3, making it possible to collect a large amount of exosomes.

What is claimed is:

1. An exosome extraction device comprising:
    a stock solution supply unit supplying an exosome-containing liquid comprising a cell culture supernatant containing exosomes;
    a first storage unit fluidly connected to the stock solution supply unit, the first storage unit storing, in an inside thereof, the exosome-containing liquid supplied from the stock solution supply unit;
    a positive pressure load unit fluidly connected to the first storage unit and configured for applying a positive pressure to the inside of the first storage unit;
    a first filter provided between the stock solution supply unit and the first storage unit and having a hole diameter that passes exosomes and blocks cells, the exosome extraction device being configured to supply the exosome-containing liquid from the stock solution supply unit to the first storage unit through the first filter;
    a second filter having a hole diameter that blocks exosomes, the second filter having a pre-filtration chamber and a post-filtration chamber;
    a circulation path comprising a supply path and a return path fluidly interconnecting the first storage unit and the pre-filtration chamber of the second filter, the exosome extraction device being configured to circulate the exosome-containing liquid stored in the first storage unit between the first storage unit and the second filter, so that the exosome-containing liquid flows from the first storage unit through the supply path to the pre-filtration chamber, and then from the pre-filtration chamber through the return path and back to the first storage unit to concentrate the exosome-containing liquid, the post-filtration chamber collecting and storing filtered liquid from the exosome-containing liquid;
    a discharge path fluidly connected to the post-filtration chamber of the second filter for discharging the filtered liquid from the post-filtration chamber;
    a second storage unit fluidly connected to the post-filtration chamber of the second filter through the discharge path;
    a recovery unit fluidly connected to the first storage unit for recovering the concentrated exosome-containing liquid stored in the first storage unit;
    a third filter provided between the first storage unit and the recovery unit and having a hole diameter that passes exosomes and blocks bacteria, the exosome extraction device being configured to supply the concentrated exosome-containing liquid, returned to the first storage unit from the pre-filtration chamber via the return path and stored in the first storage unit, to the recovery unit through the third filter;
    a steam supply unit fluidly connect to the first storage unit, the exosome extraction device being configured to supply steam from the steam supply unit to the first storage unit and from the first storage unit to the first filter and the third filter to sterilize the first filter and the third filter; and
    a chemical supply unit fluidly connected to the second storage unit, the exosome extraction device being configured to supply a cleaning chemical agent from the chemical supply unit to the second storage unit and from the second storage unit to the second filter to clean the second filter.

2. The exosome extraction device according to claim 1, further comprising a pump disposed in a fluid communication path between the stock solution supply unit and the first storage unit, the pump being disposed upstream of the first filter.

3. The exosome extraction device according to claim 2, wherein the pump is a first pump and the exosome extraction device further comprises a second pump disposed in the supply path upstream of the second filter.

4. The exosome extraction device according to claim 3, wherein the first storage unit and the recovery unit are connected by a fluid communication path connected to the supply path between the second pump and the second filter, the third filter being disposed in the fluid communication path interconnecting the first storage unit and the recovery unit.

5. The exosome extraction device according to claim 4, further comprising a controller configured to control fluid flow between: the stock solution supply unit and the first storage unit; the first storage unit and the second filter; and the first storage unit and the recovery unit.

6. The exosome extraction device according to claim 1, wherein the positive pressure load unit is configured to apply a positive pressure greater than atmospheric pressure to the inside of the first storage unit to prevent contamination of the first storage unit by external bacteria.

* * * * *